(12) United States Patent
Bouhrara et al.

(10) Patent No.: US 11,454,595 B2
(45) Date of Patent: Sep. 27, 2022

(54) SYSTEMS AND METHODS FOR EVALUATING A STRUCTURAL HEALTH OF COMPOSITE COMPONENTS BY CORRELATING POSITIONS OF DISPLACED NANOPARTICLES

(71) Applicant: Saudi Arabian Oil Company, Dhahran (SA)

(72) Inventors: Mohamed Bouhrara, El Jadida (MA); Hassan Almousa, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 243 days.

(21) Appl. No.: 16/705,487

(22) Filed: Dec. 6, 2019

(65) Prior Publication Data

US 2021/0172880 A1 Jun. 10, 2021

(51) Int. Cl.
*G01N 21/88* (2006.01)
*G06T 7/00* (2017.01)
*G06T 7/246* (2017.01)

(52) U.S. Cl.
CPC ......... *G01N 21/8851* (2013.01); *G06T 7/001* (2013.01); *G06T 7/248* (2017.01); *G01N 2021/8887* (2013.01); *G06T 2207/30252* (2013.01)

(58) Field of Classification Search
CPC ........ G01N 21/8851; G01N 2021/8887; G06T 7/001; G06T 2207/30252; G06T 7/248
See application file for complete search history.

(56) References Cited

U.S. PATENT DOCUMENTS

| 7,379,845 B2 | 5/2008 | Gorinevsky et al. |
| 7,921,727 B2 | 4/2011 | Rice |

(Continued)

FOREIGN PATENT DOCUMENTS

| CN | 103901003 A | 7/2014 |
| EP | 2431156 B1 | 5/2017 |

(Continued)

OTHER PUBLICATIONS

Dattoma, V., F. W. Panella, A. Pirinu and Andrea Saponaro. "Advanced NDT Methods and Data Processing on Industrial CFRP Components." Applied Sciences 9 (2019): 393. (Year: 2019).*

(Continued)

*Primary Examiner* — Michael Robert Cammarata
(74) *Attorney, Agent, or Firm* — Dinsmore & Shohl LLP

(57) ABSTRACT

Systems and methods for determining a damage value of one or more composite components and/or a vehicle using digital image correlation are disclosed. Digital image correlation is used to evaluate a displacement of one or more nanoparticles that are deposited on and/or embedded within the composite component. Digital image correlation is performed by identifying a first reference entry indicating a reference position of the one or more nanoparticles and correlating the first reference entry with sensor data of the composite component indicating a position of the one or more nanoparticles. The damage value of the composite component is determined based on the digital image correlation between the sensor data and the first reference entry.

18 Claims, 9 Drawing Sheets

(56) References Cited

U.S. PATENT DOCUMENTS

| | | | |
|---|---|---|---|
| 7,925,452 B2* | 4/2011 | Safai | G01N 17/00 |
| | | | 702/34 |
| 8,100,020 B2 | 1/2012 | Kinlen et al. | |
| 8,355,830 B2 | 1/2013 | Kordonowy | |
| 8,929,411 B1* | 1/2015 | Safai | G01N 17/006 |
| | | | 372/24 |
| 10,234,347 B1 | 3/2019 | Khizroev et al. | |
| 2004/0213443 A1* | 10/2004 | Haussecker | B82Y 35/00 |
| | | | 382/128 |
| 2006/0253942 A1* | 11/2006 | Barrera | G01L 1/2293 |
| | | | 73/661 |
| 2010/0213387 A1* | 8/2010 | Safai | B82Y 15/00 |
| | | | 250/458.1 |
| 2012/0007607 A1* | 1/2012 | Lowe | H04Q 9/00 |
| | | | 324/639 |
| 2017/0241992 A1* | 8/2017 | Muller-Spath | G01N 30/8658 |
| 2017/0276614 A1* | 9/2017 | Bovero | G01L 1/00 |
| 2018/0005362 A1* | 1/2018 | Wang | G06T 7/001 |
| 2018/0045574 A1* | 2/2018 | Engelbart | G01J 5/0887 |
| 2018/0118901 A1 | 5/2018 | Harper et al. | |
| 2018/0328722 A1* | 11/2018 | Bovero | G01M 11/081 |
| 2018/0340858 A1 | 11/2018 | Jahanbin et al. | |
| 2019/0147585 A1* | 5/2019 | Hartman | B33Y 99/00 |
| | | | 382/141 |
| 2019/0202738 A1* | 7/2019 | Li | C04B 18/08 |
| 2019/0250107 A1* | 8/2019 | Sreenivasan | G01N 21/21 |
| 2019/0300759 A1* | 10/2019 | Prakash | C09J 11/06 |
| 2020/0340802 A1* | 10/2020 | Tyson, II | G01M 5/0016 |
| 2022/0161298 A1* | 5/2022 | Kumar | B07C 5/342 |

FOREIGN PATENT DOCUMENTS

| | | | |
|---|---|---|---|
| WO | 2013158933 A1 | 10/2013 | |
| WO | WO-2021110735 A1 * | 6/2021 | A61K 49/0041 |

OTHER PUBLICATIONS

W. H. Peters and W. F. Ranson "Digital Imaging Techniques in Experimental Stress Analysis," Optical Engineering 21(3), 213427 (Jun. 1, 1982). https://doi.org/10.1117/12.7972925 (Year: 1982).*

Hild F, Bouterf A, Roux S. Damage measurements via DIC. Int J Fract 2015;191:77-105. (Year: 2015).*

Wang {Li, Y.; Wang, K.; Su, Z. Dispersed Sensing Networks in Nano-Engineered Polymer Composites: From Static Strain Measurement to Ultrasonic Wave Acquisition. Sensors 2018, 18, 1398. https://doi.org/10.3390/s18051398} (Year: 2018).*

Wang B, Zhong S, Lee T-L, Fancey KS, Mi J. Non-destructive testing and evaluation of composite materials/structures: A state-of-the-art review. Advances in Mechanical Engineering. Apr. 2020. doi:10.1177/1687814020913761 (Year: 2020).*

A. Trinchi et al., "Distributed quantum dot sensors for monitoring the integrity of protective aerospace coatings," 2012 IEEE Aerospace Conference, 2012, pp. 1-9, doi: 10.1109/AERO.2012.6187252. (Year: 2012).*

Berfield, T.A., Patel, J.K., Shimmin, R.G. et al. Micro- and Nanoscale Deformation Measurement of Surface and Internal Planes via Digital Image Correlation. Exp Meeh 47, 51-62 (2007). https://doi.org/10.1007/s11340-006-0531-2 (Year: 2007).*

Reisch, A.; Klymchenko, A. S. Fluorescent Polymer Nanoparticles Based on Dyes: Seeking Brighter Tools for Bioimaging. Small 2016, 12 (15), 1968-1992 (Year: 2016).*

Lyu Y, Pu K. Recent Advances of Activatable Molecular Probes Based on Semiconducting Polymer Nanoparticles in Sensing and Imaging. Adv Sci (Weinh). 2017;4(6):1600481. Published Feb. 9, 2017. doi:10.1002/advs.201600481 (Year: 2017).*

Dong, Y., Pan, B. A Review of Speckle Pattern Fabrication and Assessment for Digital Image Correlation. Exp Meeh 57, 1161-1181 (2017). https://doi.org/10.1007/s11340-017-0283-1 (Year: 2017).*

Chen, Zhenning, et al. "A method to transfer speckle patterns for digital image correlation." Measurement science and technology 26.9 (2015): 095201. (Year: 2015).*

Hanemann T, Szabó DV. Polymer-Nanoparticle Composites: From Synthesis to Modern Applications. Materials (Basel). 2010;3(6): 3468-3517. Published May 28, 2010. doi:10.3390/ma3063468. (Year: 2010).*

Digital image correlation for surface deformation measurement: historical developments, recent advances and future goals, Bing Pan,,Published Jun. 28, 2018 • © 2018 IOP Publishing Ltd Measurement Science and Technology, vol. 29, No. 8, Bing Pan 2018 Meas. Sci. Technol. 29 082001 (Year: 2018).*

International Search Report and Written Opinion dated Sep. 8, 2020 pertaining to International application No. PCT/US2020/021166 filed Mar. 5, 2020, 13 pgs.

Mehdikhani et al., "Multi-scale digital image correlation for detection and quantification of matrix cracks in carbon fiber composite laminates in the absence and presence of voids controlled by the cure cycle" Composites Part B 154 (2018) 138-147, 10 pgs.

Galietti et al., "Strain Measurement in Composite Materials Using Embedded Strain Gauges" Article in Key Engineering Materials, Jan. 1998, 11 pgs.

Berfield et al., "Micro- and Nanoscale Deformation Measurement of Surface and Internal Planes via Digital Image Correlation" Experimental Mechanics (2007) 47: 51-62, 12 pgs.

Cai et al., "Structural Health Monitoring for Composite Materials" InTech, Chapter 3 (2012), 25 pgs.

Canal et al., "Application of digital image correlation at the microscale in fiber-reinforced composites" Composites: Part A 43 (2012) 1630-1638, 9 pgs.

Grisolia et al., "Towards wireless highly sensitive capacitive strain sensors based on gold colloidal nanoparticles" Nanoscale, 2018, 10, 10479, 9 pgs.

Hou et al., "A resistance-based damage location sensor for carbon-fibre composites" Smart Mater. Structur. 11 (2002) 966-969, 4 pgs.

Kister et al., "Self-sensing E-glass fibres" Optical Materials 21 (2003) 713-727, 15 pgs.

Leopold et al., "Influence of carbon nanoparticle modification on the mechanical and electrical properties of epoxy in small volumes" Journal of Colloid and Interface Science 506 (2017) 620-632, 13 pgs.

Li et al., "Recent applications of fiber optic sensors to health monitoring in civil engineering" Engineering Structures 26 (2004) 1647-1657, 11 pgs.

Li et al., "Dispersed Sensing Networks in Nano-Engineered Polymer Composites: From Static Strain Measurement to Ultrasonic Wave Acquisition" Department of Mechanical Engineering, sensors, 2018, 15 pgs.

Luo et al., "Fluorescent Magnetic Particle Inspection Device Based on Digital Image Processing" Proceeding of the 11th World Congress on Intelligent Control and Automation, 2014, 5 pgs.

Spada et al., "Electromagnetic Nanoparticles for Sensing and Medical Diagnostic Applications" Materials 2018, 11, 603, 21 pgs.

Starman et al., "Automated System for Magnetic Particle Inspection of Railway Wheels" Starmans electronics s.r.o., 5 pgs.

Swait et al., "A practical structural health monitoring system for carbon fibre reinforced composite based on electrical resistance" Composites Science and Technology 72 (2012) 1515-1523, 9 pgs.

Wilhelmsen "Characterization of Local Strain Fields in Cross-Ply Composites Under Transverse Loading" (2015) Article, 35 pgs.

Zhong et al., "Magnetic nanoparticle temperature imaging with a scanning magnetic particle spectrometer" Meas. Sci. Technol. 29 (2016) 115903, 9 pgs.

Starbuck et al. "Smart Onboard Inspection of High Pressure Gas Fuel Cylinders" Oak Ridge National Labratory, (Sep. 27, 1999) 13 pgs.

* cited by examiner

SYSTEMS AND METHODS FOR EVALUATING A STRUCTURAL HEALTH OF COMPOSITE COMPONENTS BY CORRELATING POSITIONS OF DISPLACED NANOPARTICLES

TECHNICAL FIELD

The present specification generally relates to systems and methods for evaluating a structural health of composite components and, more particular, to systems and methods for evaluating a structural health of composite components of a vehicle.

BACKGROUND

In recent years, composite components, such as carbon fiber reinforced plastics (CFRPs), have been incorporated into various components of a vehicle to reduce a weight of the vehicle, increase a fuel efficiency of the vehicle, and increase a rigidity of the vehicle. As a non-limiting example, at least one of a vehicle chassis, an exterior component of the vehicle, and an interior component of the vehicle includes a CFRP.

However, the anisotropic properties of CFRPs can make the CFRP components vulnerable to several damage types that are not readily discernable to the naked eye of an operator or service technician of the vehicle, such as fiber breakage, matrix cracking, and fiber-matrix delamination. Current structural health monitoring systems and methods, such as radiographic and ultrasonic inspections, are ineffective in determining several damage types of a CFRP component of the vehicle. Furthermore, embedded strain gauges comprising piezoresistive materials and fiber optic sensors, which may be used to detect various damage types, are ineffective in determining several damage types of a CFRP component of the vehicle.

SUMMARY

Accordingly, a need exists for systems and methods for detecting various damage types of the composite components of the vehicle. The present disclosure is directed to systems and methods for determining a damage value of a composite component using digital image correlation (DIC). A structural health monitoring system may identify component identification information the composite component, which includes a polymer matrix, a fiber reinforcement, and one or more nanoparticles that are at least one of deposited on the composite material and embedded within the composite material. Subsequently, the structural health monitoring system obtains sensor data of the composite component, and the sensor data indicates a position of the one or more nanoparticles. The structural health monitoring system may then identify a first reference entry in a reference database based on the component identification information, and the first reference entry indicates a reference position of the one or more nanoparticles of the composite component. The structural health monitoring system then determines a damage value of the composite component based on a digital image correlation between the sensor data and the first reference entry.

According to some aspects, a structural health monitoring method includes obtaining, using one or more processors, component identification information associated with a composite component, the composite component includes a matrix and a reinforcement. The structural health monitoring method includes obtaining, using one or more sensors, sensor data of the composite component, where the sensor data of the composite component indicates a position of one or more nanoparticles, the one or more nanoparticles are at least one of deposited on the composite component and embedded within the composite component. The structural health monitoring method includes identifying, using the one or more processors, a first reference entry of a plurality of reference entries in a reference database corresponding to the component identification information, where the first reference entry indicates a reference position of the one or more nanoparticles. The structural health monitoring method includes executing, using the one or more processors, a digital image correlation between the sensor data and the first reference entry of the plurality of reference entries. The structural health monitoring method includes determining, using the one or more processors, a damage value of the composite component based on the digital image correlation between the sensor data and the first reference entry.

According to some aspects, a system includes one or more processors and one or more non-transitory memory modules communicatively coupled to the one or more processors. The one or more non-transitory memory modules store storing machine-readable instructions that, when executed, cause the one or more processors to identify indicia associated with a composite component, the indicia including component identification information, the composite component includes a matrix and a reinforcement. The one or more non-transitory memory modules store storing machine-readable instructions that, when executed, cause the one or more processors to obtain sensor data of the composite component, where the sensor data of the composite component indicates a position of one or more nanoparticles that are at least one of deposited on the composite component and embedded within the composite component. The one or more non-transitory memory modules store storing machine-readable instructions that, when executed, cause the one or more processors to identify a first reference entry of a plurality of reference entries in a reference database based on the indicia, where the first reference entry indicates a reference position of the one or more nanoparticles. The one or more non-transitory memory modules store storing machine-readable instructions that, when executed, cause the one or more processors to execute a digital image correlation between the sensor data and the first reference entry of the plurality of reference entries. The one or more non-transitory memory modules store storing machine-readable instructions that, when executed, cause the one or more processors to determine a damage value of the composite component based on the digital image correlation between the sensor data and the first reference entry.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and are not intended to limit the subject matter defined by the claims. The following detailed description of the illustrative embodiments can be understood when read in conjunction with the following drawings, where like structure is indicated with like reference numerals and in which:

Figure 1:
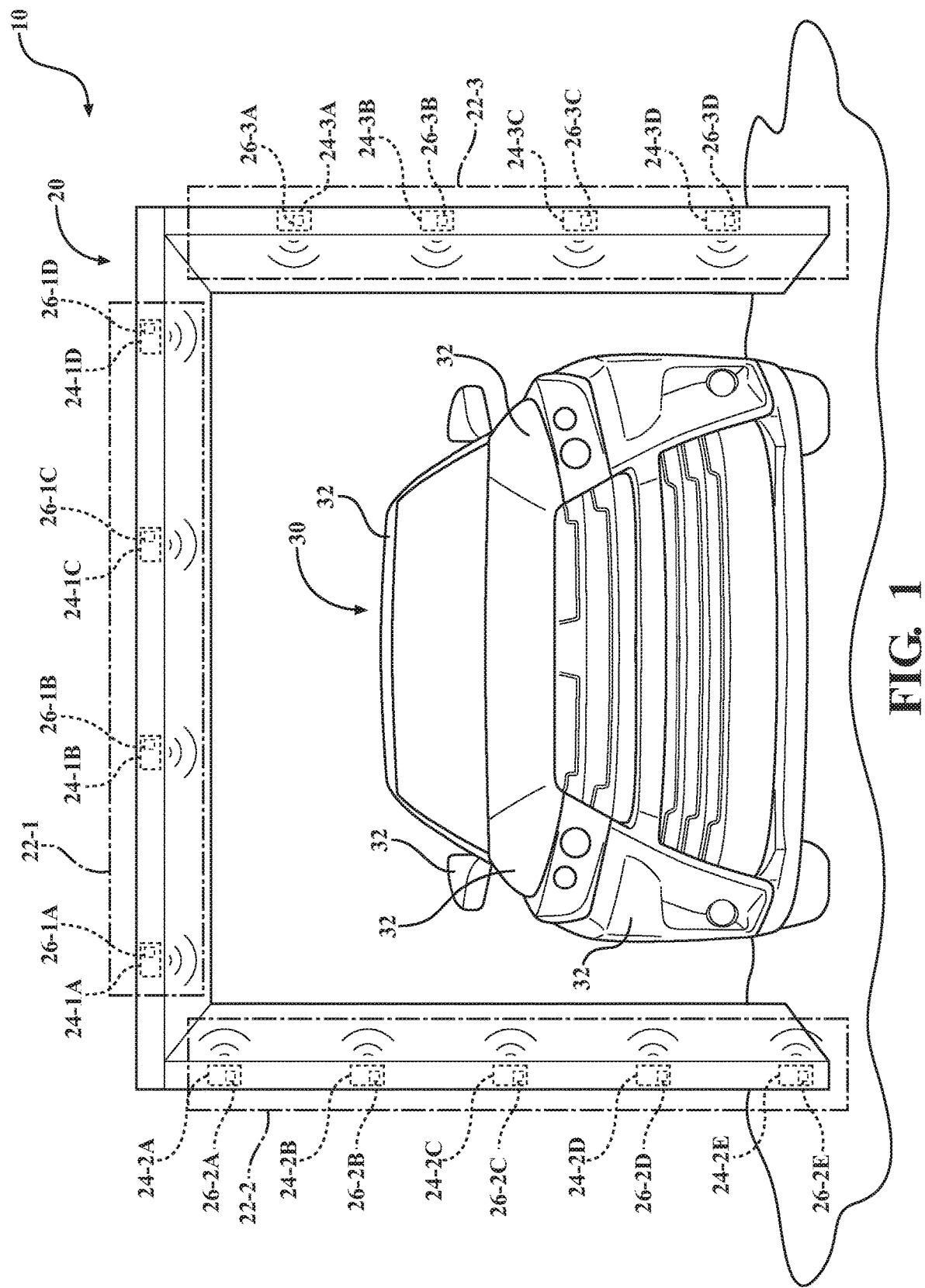
FIG. 1 schematically depicts a front view of a structural health monitoring system for monitoring the structural health of a composite component of a vehicle according to one or more embodiments shown and described herein.

For the purpose of describing the simplified schematic illustrations and descriptions of FIGS. 1-6B, a direction of an arrow, as indicated by the arrowhead, generally demonstrates the flow of information (such as data or instructions) that is of interest to the illustration. As used herein, a unidirectional arrow does not imply that no other information is transmitted between a first element and a second element. Further, for information sent from a first element to a second element, the second element may send requests for, or receipt acknowledgements of, the information to first element.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Referring generally to the figures, embodiments of the present disclosure are generally related to systems and methods for determining a damage value of a composite material using DIC. A structural health monitoring system may identify component identification information associated with the composite component, which includes a polymer matrix, a fiber reinforcement, and one or more nanoparticles that are at least one of deposited on the composite material and embedded within the composite material. As a non-limiting example, the one or more nanoparticles may be deposited on a surface of the composite material as a speckle pattern, as described below in further detail. As another non-limiting example, the one or more nanoparticles may be embedded within the composite component during a manufacturing process of the composite component, as described below in further detail.

Subsequently, the structural health monitoring system obtains sensor data of the composite component, and the sensor data indicates a position of the one or more nanoparticles. The sensor data may be obtained using one or more sensors that detect defects and/or strains of the one or more composite components, as described below in further detail.

The structural health monitoring system may then identify a first reference entry in a reference database based on the identified indicia. The first reference entry indicates a reference position of the one or more nanoparticles of the composite component. The first reference entry may be generated during a manufacturing process of the composite component and/or a vehicle in which a reference position of the one or more nanoparticles of the composite component is defined, as described below in further detail. Furthermore, the first reference entry may be generated prior to a deployment of the vehicle to an end user, as described below in further detail.

Subsequently, the structural health monitoring system then determines a damage value of the composite component based on a digital image correlation between the sensor data and the first reference entry. By executing a digital image correlation between the sensor data and the first reference entry, the structural health monitoring system may determine a displacement of the one or more nanoparticles of the composite component. The structural health monitoring system may generate a damage value based on the displacement of the one or more nanoparticles of the composite component. If the damage value is greater than a threshold value, the structural health monitoring system may transmit a corresponding notification, as described below in further detail.

Accordingly, the systems and methods described herein enable a computing system or a user thereof to accurately identify and detect damage to a composite material of a vehicle that may otherwise not be readily discernable to the naked eye of the user.

As used herein, the term "signal" means a waveform (for example, electrical, optical, magnetic, mechanical or electromagnetic waveforms) configured to travel through a medium, such as DC, AC, sinusoidal-wave, triangular-wave, square-wave, vibration, and the like.

As used herein, the phrase "shared processor circuit" refers to a single processor circuit that executes some or all of the machine-readable instructions from multiple modules of one or more non-transitory computer-readable mediums.

As used herein, the phrase "group processor circuit" refers to a processor circuit that, in combination with additional processor circuits, executes some or all of the machine-executable instructions from the multiple modules of one or more non-transitory computer-readable mediums. References to multiple processor circuits encompass multiple processor circuits on discrete dies, multiple processor circuits on a single die, multiple cores of a single processor circuit, multiple threads of a single processor circuit, or a combination of the above.

As used herein, the phrase "shared memory circuit" refers to a single memory circuit that stores some or all of the machine-readable instructions from multiple modules, which are described below in further detail.

As used herein, the phrase "group memory circuit" refers to a memory circuit that, in combination with additional memories, stores some or all machine-readable instructions from the multiple modules, which are described below in further detail.

As used herein, the term "module" may refer to, be part of, or include: an Application Specific Integrated Circuit (ASIC); a digital, analog, or mixed analog/digital discrete or integrated circuit; a combinational logic circuit; a field programmable gate array (FPGA); a processor circuit that executes machine-readable instructions; a memory circuit that stores machine-readable instructions executed by the processor circuit; other suitable hardware components that provide the described functionality; or a combination of some or all of the above.

As used herein, the phrase "magnetic nanoparticles" refers to a particle that can be manipulated by varying magnetic fields and a particle that includes a magnetic material, such as iron, nickel, cobalt, magnetite, and/or the like. The magnetic nanoparticles may have various diameters, such as greater than 0.1 nanometers, greater than 1 nanometer, greater than 2 nanometers, greater than 3 nanometers, greater than 4 nanometers, greater than 5 nanometers, greater than 6 nanometers, greater than 7 nanometers, greater than 8 nanometers, greater than 9 nanometers, or greater than 10 nanometers.

As used herein, the phrase "fluorescent polymer nanoparticles" refers to polymer particles that emit light when illuminated by electromagnetic radiation having wavelengths within a particular range, such as an ultraviolet (UV) ray having a wavelength between 10 nanometers and 400 nanometers. The fluorescent polymer nanoparticles may have various diameters, such as greater than 0.1 nanometers, greater than 1 nanometer, greater than 2 nanometers, greater than 3 nanometers, greater than 4 nanometers, greater than 5 nanometers, greater than 6 nanometers, greater than 7 nanometers, greater than 8 nanometers, greater than 9 nanometers, greater than 10 nanometers. The fluorescent polymer nanoparticle may include various fluorescent polymers, such as poly[2-methoxy-5-(2-ethylhexyloxy)-1,4-(1-cyanovinylene-1,4-phenylene)], poly[9-anthracenylmethyl acrylate], poly[9-anthracenylmethyl acrylate methacrylate], poly[fluorescein O-acrylate], and the like.

As used herein, the phrase "quantum dots" refers to core-shell semiconductor nanocrystal particles that emit light when illuminated by electromagnetic radiation having wavelengths within a particular range, such as a UV ray having a wavelength between 10 nanometers and 400 nanometers. Additionally or alternatively, the quantum dots may emit light when subjected to tension or compression forces above a threshold pressure value, such as greater than 0.5 megapascals, greater than 1 megapascals, greater than 10 megapascals, and greater than 100 megapascals. The quantum dots may have various diameters, such as greater than 0.1 nanometers, greater than 1 nanometer, greater than 2 nanometers, greater than 3 nanometers, greater than 4 nanometers, greater than 5 nanometers, greater than 6 nanometers, greater than 7 nanometers, greater than 8 nanometers, greater than 9 nanometers, or greater than 10 nanometers. The quantum dots may include various semiconductor materials, such as silicon, diamond, silicon carbide, gallium arsenide, cadmium selenide, cadmium sulfide, indium arsenide, or any other semiconductor material. It should be understood that other photochromic materials may be used in place of or in addition to the quantum dots.

As used herein, the phrase "digital image correlation" refers to an image processing method that determines the contours and/or displacements of one or more nanoparticles deposited on or embedded within a composite component with respect to a reference position of the one or more nanoparticles.

Spatial and functional relationships between elements (for example, between modules, circuit elements, semiconductor layers, etc.) are described herein using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

Referring now to FIG. 1, an example vehicle system 10 including a structural health monitoring (SHM) system 20 and a vehicle 30 are schematically depicted. In one or more embodiments, the vehicle 30 may be one of a car, a truck, a sport utility vehicle, a van, a boat, a plane, an unmanned aerial vehicle, or other vehicle types.

The vehicle 30 includes one or more composite components 32. In one or more embodiments, the composite components 32 are incorporated within a chassis of the vehicle 30, an exterior of the vehicle 30 (such as a hood of the vehicle 30, a bumper of the vehicle 30, a roof of the vehicle 30, and/or the like), and/or an interior of the vehicle 30 (such as a dash panel of the vehicle 30, a center console of the vehicle 30, and/or the like). It should be understood that the composite components 32 may be positioned at any location of the vehicle 30 in some embodiments.

Figure 2A:
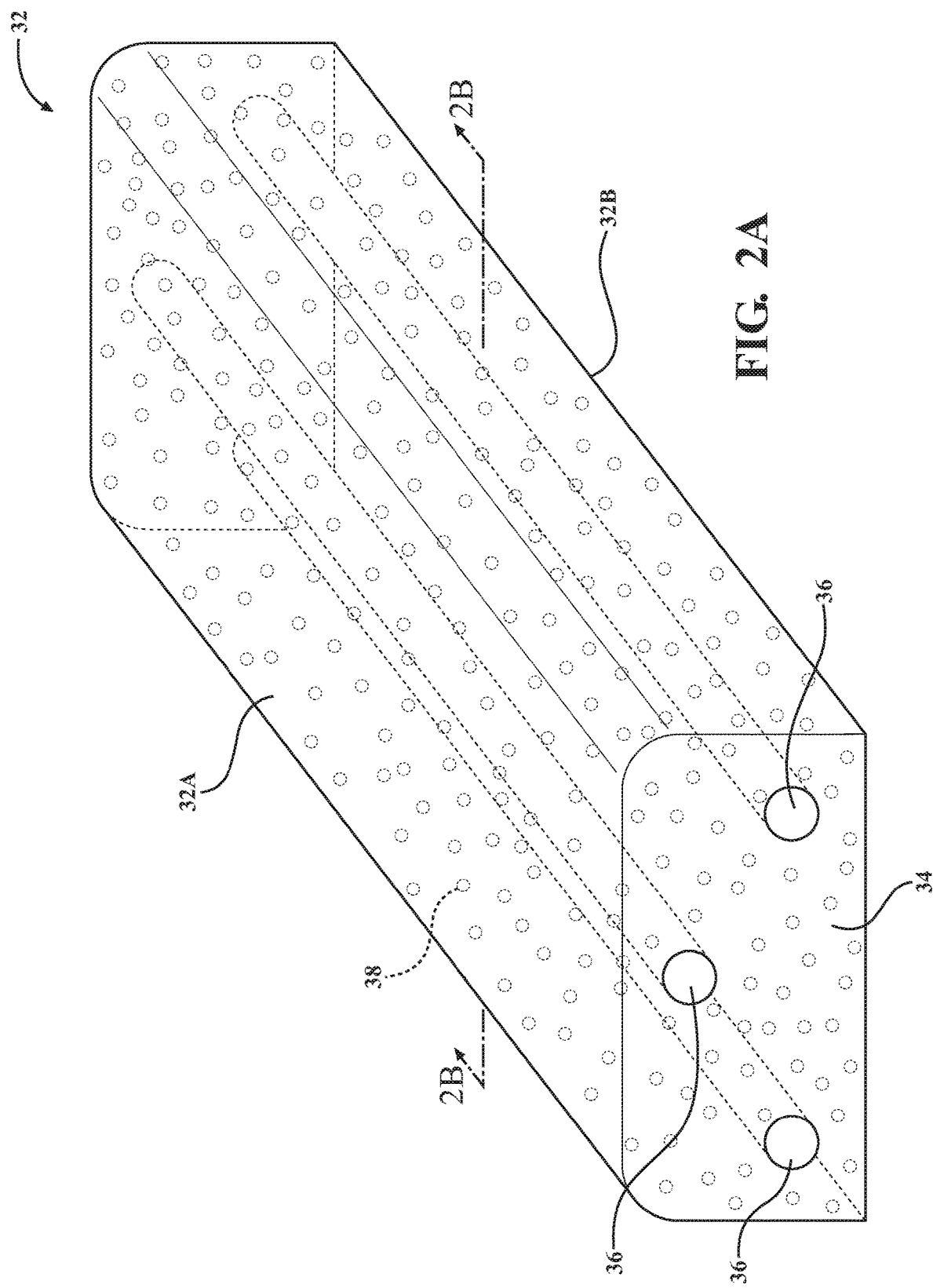
FIG. 2A schematically depicts a partial perspective view of the composite component of the vehicle according to one or more embodiments shown and described herein.
Figure 2B:
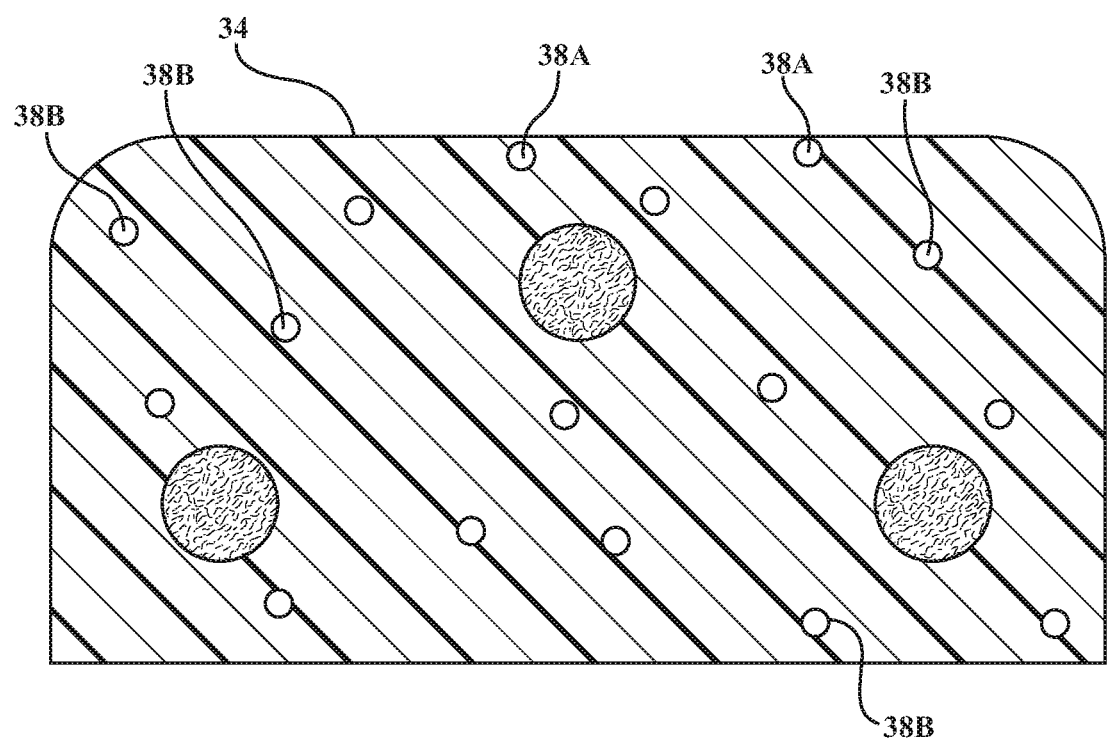
FIG. 2B schematically depicts a cross section view of the composite component illustrated in FIG. 2A along line B-B according to one or more embodiments shown and described herein.

With reference to FIGS. 1 and 2A-2B, the one or more composite components 32 may be formed of a composite material such that the one or more composite components 32 may each be a CFRP component that includes a matrix material 34 and at least one reinforcement 36. In some embodiments, the matrix material 34 is a polymer matrix, and the at least one reinforcement 36 is at least one reinforcement 36. As shown in FIG. 2B, the one or more composite components 32 each include one or more nanoparticles 38A, such as magnetic nanoparticles, fluorescent polymer nanoparticles, and quantum dots that are deposited on a first surface 32A of the one or more composite components 32, as described below in further detail. Moreover, the one or more composite components 32 may each include one or more nanoparticles 38B embedded within the one or more composite components 32, as described below in further detail. The one or more nanoparticles 38A and the one or more nanoparticles 38B may be collectively referred to hereinafter as one or more nanoparticles 38.

Referring to FIG. 1, the SHM system 20 includes a first SHM hardware subsystem 22-1, a second SHM hardware subsystem 22-2, and a third SHM hardware subsystem 22-3 (collectively referred to as SHM hardware subsystems 22). Furthermore, the first SHM hardware subsystem 22-1 includes sensor system 24-1A, sensor system 24-1B, sensor system 24-1C, and sensor system 24-1D (collectively referred to as first sensor system 24-1). The second SHM hardware subsystem 22-2 includes sensor system 24-2A, sensor system 24-2B, sensor system 24-2C, and sensor system 24-2D (collectively referred to as second sensor system 24-2). The third SHM hardware subsystem 22-3 includes sensor subsystem 24-3A, sensor system 24-3B, sensor system 24-3C, sensor system 24-3D, and sensor system 24-3E (collectively referred to as third sensor system 24-3). As used herein, the first sensor system 24-1, the second sensor system 24-2, and the third sensor system 24-3 are collectively referred to as sensor systems 24.

In some embodiments, sensor system 24-1A includes one or more sensors 26-1A, sensor system 24-1B includes one or more sensors 26-1B, sensor system 24-1C includes one or more sensors 26-1C, and sensor system 24-1D includes one or more sensors 26-1D. Furthermore, sensor system 24-2A includes one or more sensors 26-2A, sensor system 24-2B includes one or more sensors 26-2B, sensor system 24-2C includes one or more sensors 26-2C, and sensor system 24-2D includes one or more sensors 26-2D. Further, sensor system 24-3A includes one or more sensors 26-3A, sensor system 24-3B includes one or more sensors 26-3B, sensor system 24-3C includes one or more sensors 26-3C, sensor system 24-3D includes one or more sensors 26-3D, and sensor system 24-3E includes one or more sensors 26-3E. As used herein, the one or more sensors 26-1A, the one or more sensors 26-1B, the one or more sensors 26-1C, the one or more sensors 26-1D, the one or more sensors 26-2A, the one or more sensors 26-2B, the one or more sensors 26-2C, the one or more sensors 26-2D, the one or more sensors 26-3A, the one or more sensors 26-3B, the one or more sensors 26-3C, the one or more sensors 26-3D, and the one or more sensors 26-3E are collectively referred to as one or more sensors 26.

In various embodiments, the one or more sensors 26 may detect defects and/or strains of the one or more composite components 32 of the vehicle 30 based on a displacement of the nanoparticles 38, as described in greater detail below. As a non-limiting example, the sensor systems 24 include one or more imaging sensors, such as a camera. As another non-limiting example, the sensor systems 24 include one or more sensors 26 that obtain a light intensity value of the one or more composite components 32 (a radiant intensity, luminous intensity, an irradiance, a radiance, and/or the like), such as a photometer, a photosensitive sensor, and/or other sensors that obtain light intensity values of the one or more composite components 32. It should be understood that the one or more sensors 26 may be any sensor that detects defects and/or strains of the one or more composite components 32 based on a displacement of the nanoparticles 38.

In one or more embodiments, the sensor systems 24 include hardware that operate in conjunction with the one or more sensors 26. As a non-limiting example, when the one or more sensors 26 include one or more cameras that obtain image data of the one or more composite components 32, the sensor systems 24 may include a UV light source that provides an electromagnetic wave to the one or more composite components 32. Accordingly, the one or more nanoparticles 38, which may include fluorescent polymer nanoparticles and quantum dots, may emit light in response to receiving the electromagnetic wave from the UV light source, thereby enabling the one or more cameras to obtain image data of the one or more nanoparticles 38.

As another non-limiting example, when the one or more sensors 26 include one or more cameras that obtain image data of the one or more composite components 32, the sensor systems 24 may include an actuation device that induces a stress in the one or more composite components 32. Accordingly, the one or more nanoparticles 38, which may be quantum dots, may emit light in response to the induced stress, thereby enabling the one or more cameras to obtain image data of the one or more nanoparticles 38.

As yet another non-limiting example, when the one or more sensors 26 include one or more cameras that obtain image data of the one or more composite components 32, the sensor systems 24 may include an electrical actuation device that varies a magnetic field proximate to the one or more composite components 32. Accordingly, the one or more nanoparticles 38, which may be magnetic nanoparticles, may emit light in response to the varying magnetic fields, thereby enabling the one or more cameras to obtain image data of the one or more nanoparticles 38.

In various embodiments, the SHM system 20 determines whether the one or more composite components 32 of the vehicle 30 are damaged by obtaining sensor data of the one or more composite components 32, identifying a corresponding reference entry in a reference database, executing a digital image correlation between the sensor data and the reference entry, and determining a damage value of the one or more composite components 32 of the vehicle 30, as discussed in greater detail below.

With reference to FIG. 2A, an example embodiment of the one or more composite components 32 is schematically depicted. In various embodiments, each of the one or more composite components 32 includes the first surface 32A and a second surface 32B, the matrix material 34, the at least one reinforcements 36, and the one or more nanoparticles 38 deposited on the first surface 32A of the one or more composite components 32.

In one or more embodiments, the matrix material 34 includes one or more polymers or combinations of polymers, such as a resin (nylon, polyester, polyurethane, vinyl, vinyl ester, epoxy, and/or the like). In one or more embodiments, the at least one reinforcements 36 are a fiber material. It should be understood that the at least one reinforcements 36 may include other fiber types in some embodiments, such as a carbon fiber, a glass fiber, an aramid fiber, and/or the like. As described above, the one or more nanoparticles 38 may include one or more magnetic nanoparticles, fluorescent polymer nanoparticles, and/or quantum dots.

The one or more composite components 32 may be formed using various manufacturing processes. As a non-limiting example, a precursor, such as polyacrylonitrile (PAN), rayon, or petroleum pitch, are drawn into long fibers. The fibers may then be chemically altered to stabilize bonding, and the stabilized fibers may be heated to form a plurality of bonded carbon crystals. The surface of the fibers may then be oxidized, coated, and wound onto bobbins to form the at least one reinforcements 36. Subsequently, the at least one reinforcements 36 may be bonded with the matrix material 34 by, for example, vacuum-bagging and curing the at least one reinforcements 36 and the matrix material 34. It should be understood that any suitable process may be performed to form the composite components 32 having the matrix material 34 and the at least one reinforcements 36 in some embodiments.

As described above, the one or more nanoparticles 38 may be deposited onto the first surface 32A of the one or more composite components 32. As a non-limiting example, the one or more nanoparticles 38 may be deposited on the first surface 32A of the one or more composite components 32 in a speckle pattern. As a non-limiting example, the one or more nanoparticles 38 may be sprayed onto the first surface 32A of the one or more composite components 32. As another non-limiting example, the one or more nanoparticles 38 may be deposited onto the first surface 32A of the one or more composite components 32 using a spin coating process. It should be understood that any suitable process may be performed to deposit the one or more nanoparticles 38 onto the first surface 32A of the one or more composite components 32 in some embodiments.

As illustrated in FIG. 2B, which is a cross section view of the composite component 32 along line B-B illustrated in FIG. 2A, the one or more nanoparticles 38 are embedded within the matrix material 34 of the one or more composite components 32. As a non-limiting example, the one or more nanoparticles 38 may be embedded within each of the one or more composite components 32 during the bonding of the at least one reinforcements 36 and the matrix material 34.

Figure 3A:
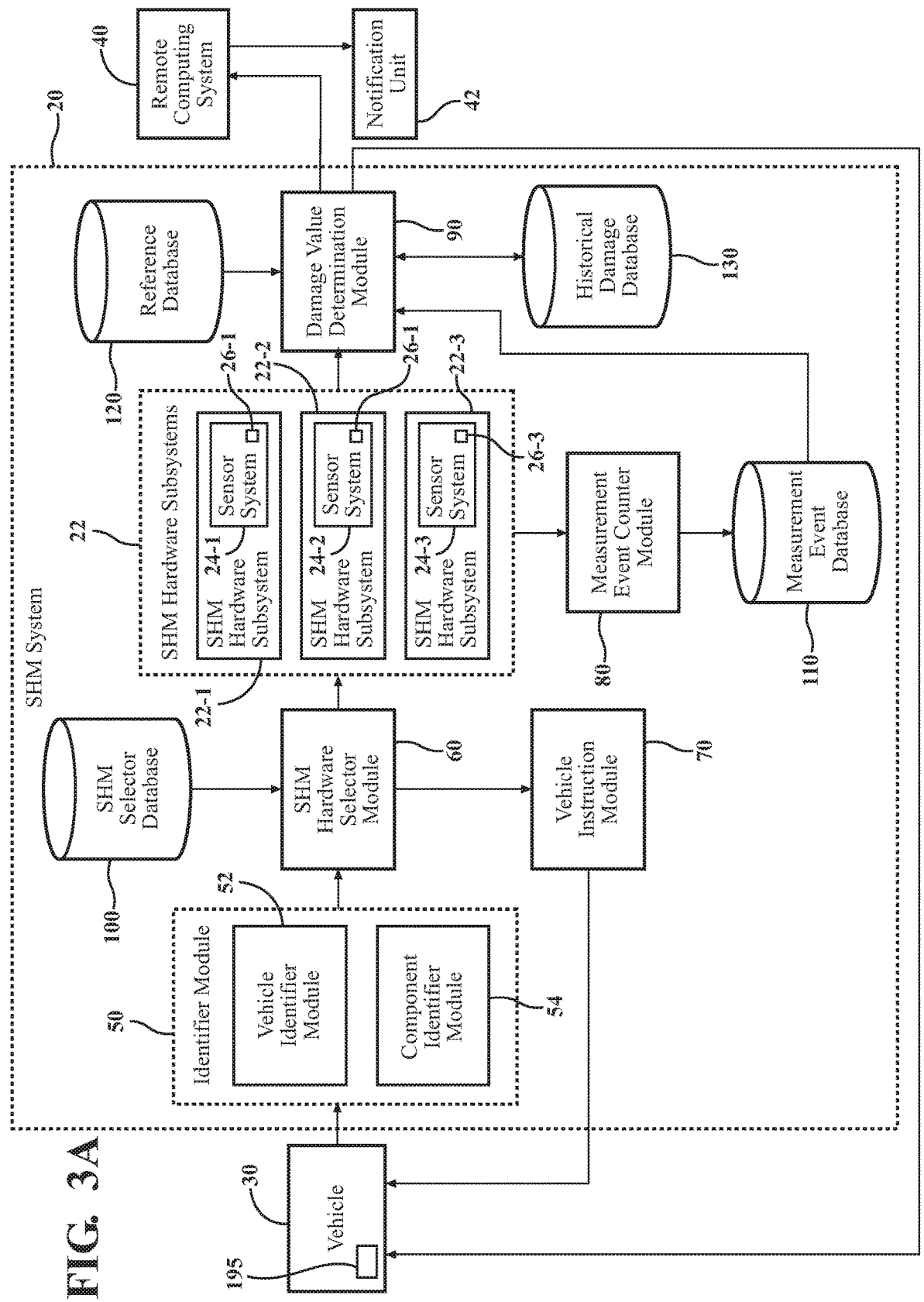
FIG. 3A schematically depicts a functional block diagram of the structural health monitoring system and the vehicle of FIG. 1 according to one or more embodiments shown and described herein.

With reference to FIG. 3A, an example embodiment of the SHM system 20 is schematically depicted showing additional components contained therein. In one or more embodiments, the SHM system 20 includes an identifier module 50, an SHM hardware selector module 60, a vehicle instruction module 70, a measurement event counter module 80, a damage value determination module 90, an SHM selector database 100, a measurement event database 110, a reference database 120, and a historical damage database 130. In one or more embodiments, the identifier module 50 includes a vehicle identifier module 52 and a component identifier module 54. While the measurement event database 110, the reference database 120, and the historical damage database 130 are shown as components of the SHM system 20, in some embodiments, at least one of the measurement event database 110, the reference database 120, and the historical damage database 130 may be located externally to the SHM system 20.

The identifier module 50 is communicatively coupled to the vehicle 30 and the SHM hardware selector module 60. The SHM hardware selector module 60 is communicatively coupled to the SHM selector database 100 and the vehicle instruction module 70. The vehicle instruction module 70 is communicatively coupled to the SHM hardware selector module 60 and the vehicle 30. The measurement event counter module 80 is communicatively coupled to the SHM hardware subsystems 22 and the measurement event database 110. The damage value determination module 90 is communicatively coupled to the SHM hardware subsystems 22, the measurement event database 110, the reference database 120, the historical damage database 130, and a remote computing system 40.

Figure 3B:
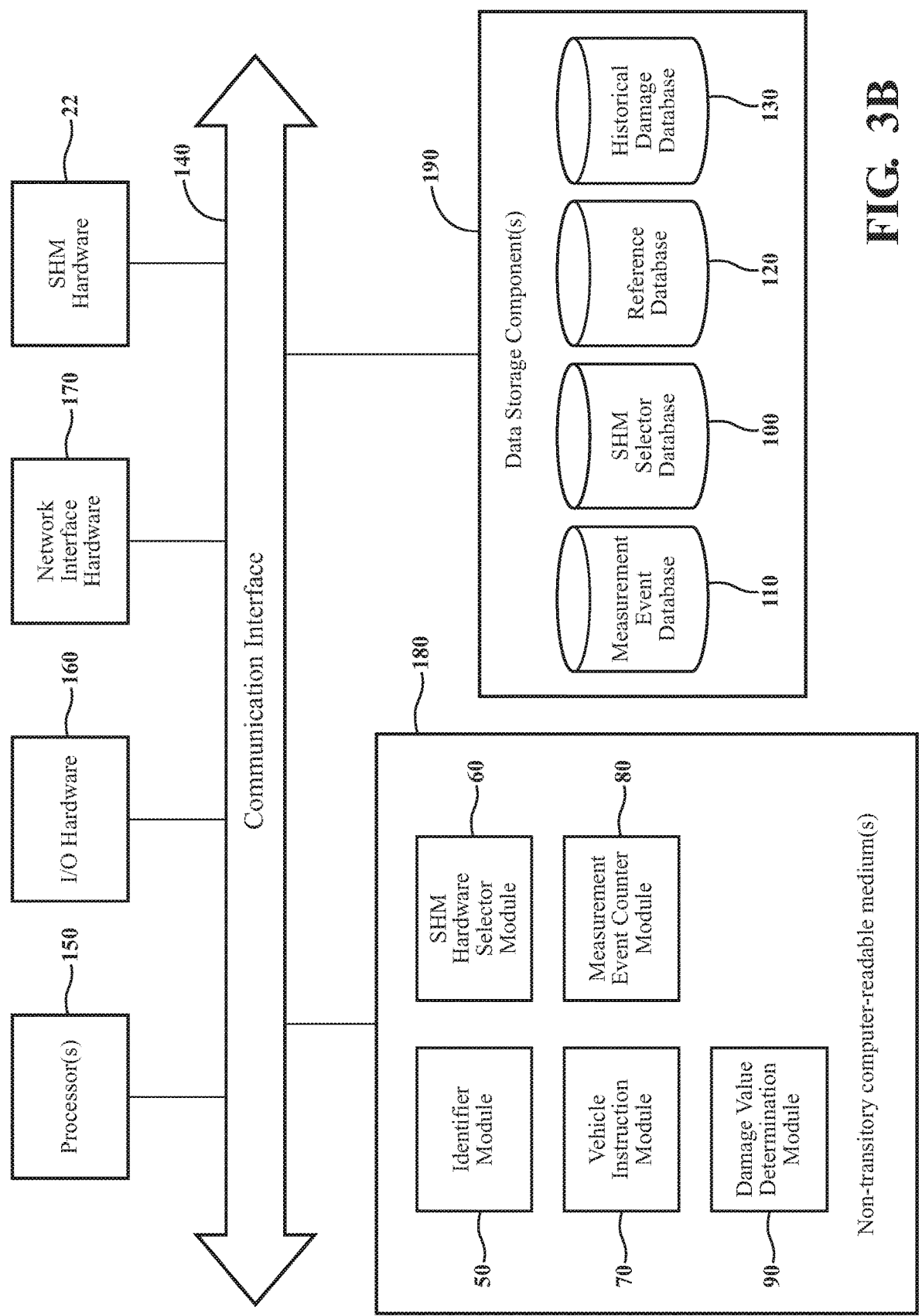
FIG. 3B schematically depicts a functional block diagram of modules and components contained within the structural health monitoring system of FIG. 3A according to one or more embodiments shown and described herein.

With reference to FIG. 3B, an example embodiment of the SHM system 20 is schematically depicted showing additional hardware components contained therein. The SHM system 20 generally includes the SHM hardware subsystems 22, a communication interface 140, one or more processors 150, input/output hardware 160, network interface hardware 170, one or more non-transitory computer-readable mediums 180, and one or more data storage components 190. The components of the SHM system 20 are physically and/or communicatively coupled through the communication interface 140.

The communication interface 140 is formed from any medium that is configured to transmit a signal. As non-limiting examples, the communication interface 140 is formed of conductive wires, conductive traces, optical waveguides, or the like. The communication interface 140 may also refer to the expanse in which electromagnetic radiation and their corresponding electromagnetic waves are propagated. Moreover, the communication interface 140 may be formed from a combination of mediums configured to transmit signals. In one embodiment, the communication interface 140 includes a combination of conductive traces, conductive wires, connectors, and buses that cooperate to permit the transmission of electrical data signals to and from the various components of the SHM system 20.

The one or more processors 150, each of which may be a computer processing unit (CPU), receive and execute machine-readable instructions stored in the one or more non-transitory computer-readable mediums 180. As a non-limiting example, the one or more processors 150 may be one of a shared processor circuit, dedicated processor circuit, or group processor circuit.

The input/output hardware 160 may include a basic input/output system (BIOS) that interacts with hardware of the SHM system 20, device drivers that interact with particular devices of the SHM system 20, one or more operating systems, user applications, background services, background applications, etc.

The network interface hardware 170 may include and/or be configured to communicate with any wired or wireless networking hardware, including an antenna, a modem, a LAN port, a wireless fidelity (Wi-Fi) card, a WiMax card, a long term evolution (LTE) card, a ZigBee card, a Bluetooth chip, a USB card, mobile communications hardware, and/or other hardware for communicating with other networks and/or devices.

The one or more data storage components 190, which include the SHM selector database 100, the measurement event database 110, the reference database 120, and the historical damage database 130, are communicatively coupled to the one or more processors 150. As a non-limiting example, the one or more data storage components 190 may include one or more database servers that support NoSQL, MySQL, Oracle, SQL Server, NewSQL, and/or the like.

The one or more non-transitory computer-readable mediums 180 are communicatively coupled to the one or more processors 150. As a non-limiting example, the one or more non-transitory computer-readable mediums 180 may be one of a shared memory circuit, dedicated memory circuit, or group memory circuit. Non-limiting examples of the one or more non-transitory computer-readable mediums 180 include random access memory (including SRAM, DRAM, and/or other types of random access memory), read-only memory (ROM), flash memory, registers, compact discs (CD), digital versatile discs (DVD), and/or other types of storage components.

A description of the various modules of the SHM system 20 will now be provided with reference to FIGS. 3A-3B.

The identifier module 50 identifies the vehicle 30 and/or the one or more composite components 32 of the vehicle 30 based on identifying indicia 195 of the vehicle 30 and/or the one or more composite components 32 of the vehicle 30 and outputs the identification to the SHM hardware selector module 60, as described below in further detail with reference to FIGS. 4-5.

The SHM hardware selector module 60 selectively activates one of the SHM hardware subsystems 22 based on the identification output by the identifier module 50 and outputs the selection to the vehicle instruction module 70, as described below in further detail with reference to FIGS. 4-5.

In some embodiments, the vehicle instruction module 70 may instruct an operator of the vehicle 30 to perform certain maneuvers and/or operations based on the selection of one of the SHM hardware subsystems 22, as described below in further detail with reference to FIGS. 4-5.

The measurement event counter module 80 generates and outputs a testing iteration value of the vehicle 30 and/or the one or more composite components 32 of the vehicle 30, as described below in further detail with reference to FIGS. 4-5.

The damage value determination module 90 determines a damage value of the vehicle 30 and/or the one or more composite components 32 of the vehicle 30 based on a displacement of the one or more nanoparticles 38 deposited on and/or embedded within the composite components 32 of the vehicle 30, as described below in further detail with reference to FIGS. 4-5. In one or more embodiments, the damage value determination module 90 outputs the damage value to the remote computing system 40.

A description of the various databases of the SHM system 20 will now be provided with reference to FIGS. 3A-3B. The SHM selector database 100 includes a plurality of entries that correlates the one or more nanoparticles 38 of the one or more composite components 32 and/or the vehicle 30 to a corresponding SHM hardware subsystem 22. The measurement event database 110 includes a plurality of entries that indicate a testing iteration value of the one or more composite components 32 and/or the vehicle 30. The reference database 120 includes a plurality of reference entries obtained during a manufacturing process of the one or more composite components 32 and/or the vehicle 30. The historical damage database 130 includes a plurality of entries indicating expected displacement values based on a testing iteration value of the one or more composite components 32 and/or the vehicle 30. The SHM selector database 100, the measurement event database 110, the reference database 120, and the historical damage database 130 are described below in further detail with reference to FIGS. 4-5.

Figure 4:
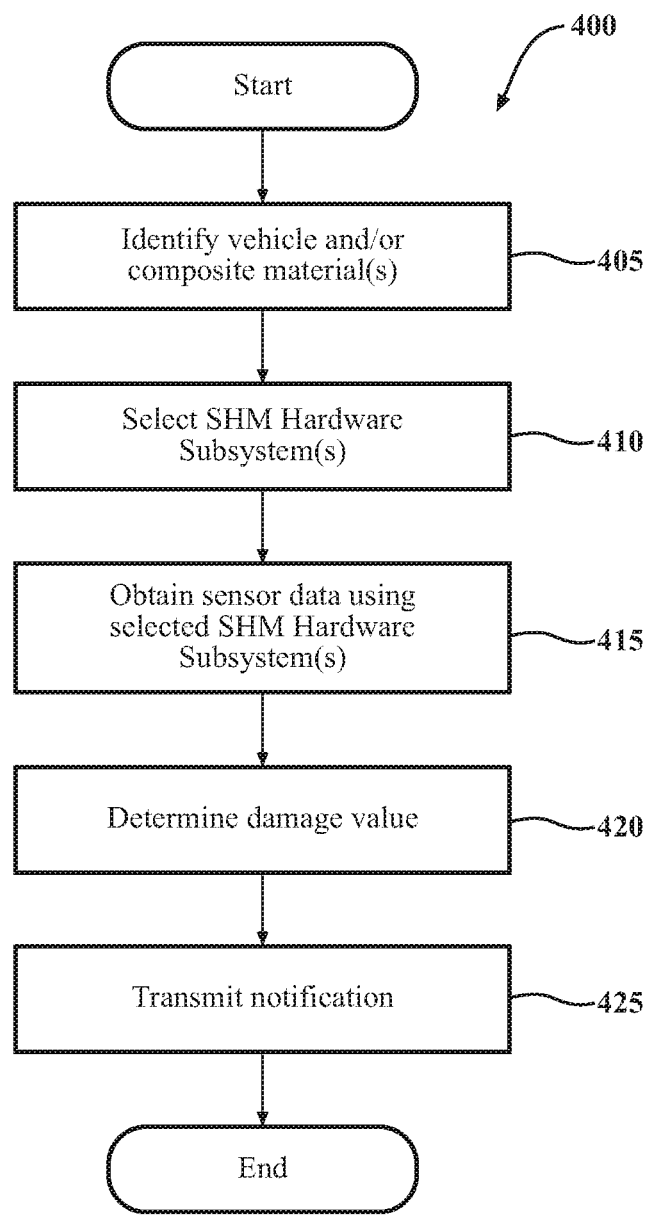
FIG. 4 schematically depicts a flow diagram illustrating an example method for detecting damage to a composite material of a vehicle according to one or more embodiments shown and described herein.

With reference to FIG. 4, a flow diagram illustrating example method 400 for detecting damage of the one or more composite components 32 and/or the vehicle 30 is schematically depicted. The flow diagram elements described in FIG. 4 may be translated into machine-readable instructions. As non-limiting examples, the machine-readable instructions may be written using any programming protocol, such as: descriptive text to be parsed (for example, such as hypertext markup language, extensible markup language, etc.), (ii) assembly language, (iii) object code generated from source code by a compiler, (iv) source code written using syntax from any suitable programming language for execution by an interpreter, (v) source code for compilation and execution by a just-in-time compiler, etc. Alternatively, the machine-readable instructions may be written in a hardware description language, such as logic implemented via either an FPGA configuration or an ASIC, or their equivalents. Accordingly, the functionality described herein may be implemented in any conventional computer programming language, as pre-programmed hardware elements, or as a combination of hardware and software components.

While the blocks shown in FIG. 4 are shown as all-occurring and in a particular order, in other embodiments, one or more of the blocks may not be performed, and in some embodiments, one or more of the blocks may be performed in a different order as shown and described herein.

Referring to FIG. 4 in conjunction with FIGS. 1, 2A-2B, and 3A-3B, at block 405, the identifier module 50 of the SHM system 20 identifies the vehicle 30 and/or the one or more composite components 32 based on identifying indicia 195 of the vehicle 30 and/or the one or more composite components 32. As a non-limiting example, the vehicle identifier module 52 of the identifier module 50 may obtain image data of the identifying indicia 195 of the vehicle 30 using an imaging device. The identifying indicia 195 may include a vehicle identification number (VIN), a bar code, an RFID tag, a make of the vehicle 30, a model of the vehicle 30, a shape of the vehicle 30, and/or other distinguishing characteristic of the vehicle 30. Subsequently, the vehicle identifier module 52 of the identifier module 50 may execute various image processing algorithms to identify the vehicle 30. As a non-limiting example, the vehicle identifier module 52 may obtain an image of a VIN of the vehicle 30 and identify, using an image processing algorithm, the vehicle 30 based on the VIN.

Furthermore, the component identifier module 54 of the identifier module 50 may scan the identifying indicia 195 of one or more composite components 32. Subsequently, the component identifier module 54 of the identifier module 50 may determine, based on the scanned data, a type of the one or more composite components 32 and any distinguishing characteristics associated with the one or more composite components 32, such as a geometry, dimensions, color, component type, nanoparticle type, and so on. As a non-limiting example, the component identifier module 54 may scan an RFID tag of the vehicle 30 and/or the one or more composite components 32 and identify that the composite component 32 is a vehicle chassis including a plurality of quantum dots based on the scanned RFID tag.

Accordingly, the identifier module 50 may generate component identification information by correlating the vehicle 30 identified by the vehicle identifier module 52 with the composite component 32 identified by the component identifier module 54. The component identification information may identify a particular composite component 32 of the identified vehicle 30, the type of the one or more nanoparticles 38 deposited on and/or embedded within the particular composite component 32, and a first reference entry associated with the particular composite component 32 of the identified vehicle 30, as discussed in greater detail below. Moreover, the identifier module 50 may provide the component identification information to the SHM hardware selector module 60.

Still referring to FIG. 4 in conjunction with FIGS. 1, 2A-2B, and 3A-3B, at block 410, the SHM hardware selector module 60 of the SHM system 20 selects one of the SHM hardware subsystems 22. As described above, the SHM hardware selector module 60 may receive the component identification information from the identifier module 50. Moreover, the SHM hardware selector module 60 may determine that the nanoparticle type of the one or more composite components 32 (that is, the type of the one or more nanoparticles 38 embedded in and/or deposited on the one or more composite components 32) is a plurality of quantum dots based on the component identification information. Accordingly, the SHM hardware selector module 60 may retrieve a first entry of the plurality of entries of the SHM selector database 100, where the first entry includes information that correlates the nanoparticle type to one of the SHM hardware subsystems 22, such as the first SHM hardware subsystem 22-1. Accordingly, the first SHM hardware subsystem 22-1 includes a corresponding sensor system 24 for obtaining sensor data indicating the displacement of the plurality of quantum dots, as described below in further detail. It should be understood that the plurality of entries of the SHM selector database 100 may include information that correlates other component identification information, such as a particular composite component 32 of the identified vehicle 30 and/or a first reference entry associated with the particular composite component 32 of the identified vehicle 30.

Still referring to FIG. 4 in conjunction with FIGS. 1, 2A-2B, and 3A-3B, at block 415, the corresponding sensor systems 24 of the selected SHM hardware subsystems 22

(the first SHM hardware subsystem 22-1) obtain sensor data of the one or more composite components 32. As a non-limiting example and as described above, the first SHM hardware subsystems 22-1 may include a UV light source that provides an electromagnetic wave to the one or more composite components 32. Accordingly, if the one or more nanoparticles 38 are fluorescent polymer nanoparticles and/or the quantum dots, one or more cameras of the first sensor system 24-1 may capture the light emitted by the one or more nanoparticles 38 and determine the corresponding position of the one or more nanoparticles 38 within and/or on the one or more composite components 32 based on the corresponding image data.

Still referring to FIG. 4 in conjunction with FIGS. 1, 2A-2B, and 3A-3B, at block 420, the damage value determination module 90 determines a damage value of the one or more composite components 32. As described below in further detail with reference to FIG. 5, the damage value determination module 90 may determine the damage value based on a displacement of the one or more nanoparticles 38 and an entry from at least one of the measurement event database 110, the reference database 120, and the historical damage database 130.

Still referring to FIG. 4 in conjunction with FIGS. 1, 2A-2B, and 3A-3B, at block 425, the damage value determination module 90 transmits a notification corresponding to the determined damage value. In one or more embodiments, the notification may be transmitted to a remote computing system 40, and the remote computing system 40 may cause a notification unit 42, which may include a display, an auditory circuit, and/or a haptic circuit, to generate at least one of a visual notification, audio notification, and/or haptic notification in response to receiving the notification.

Figure 5:
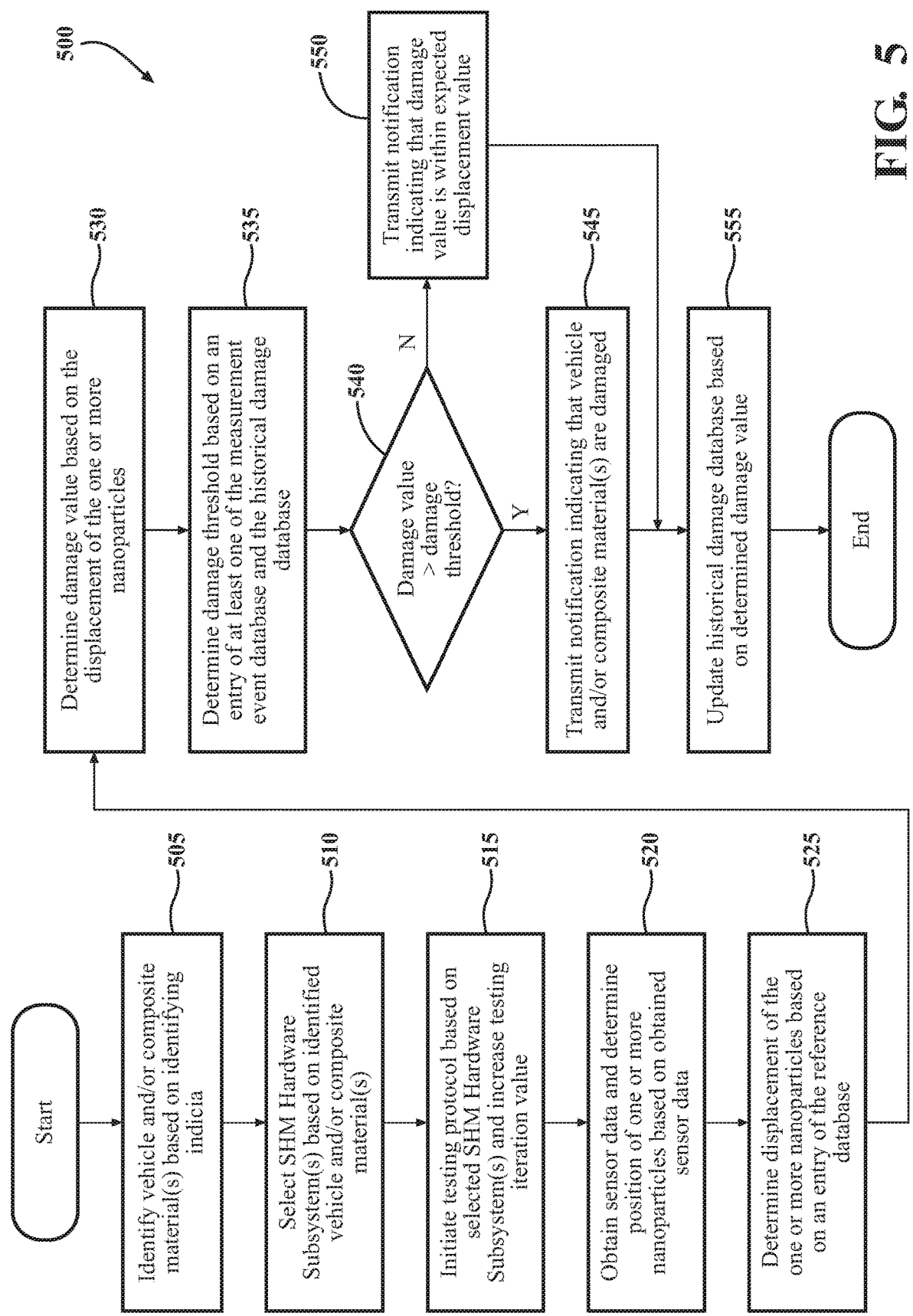
FIG. 5 schematically depicts a flow diagram illustrating another example method for detecting damage to a composite material of a vehicle according to one or more embodiments shown and described herein.

With reference to FIG. 5, a flow diagram illustrating example method 500 for detecting damage of the one or more composite components 32 and/or the vehicle 30 is schematically depicted. The flow diagram elements described in FIG. 5 may be translated into machine-readable instructions. As non-limiting examples, the machine-readable instructions may be written using any programming protocol, such as: descriptive text to be parsed (for example, such as hypertext markup language, extensible markup language, etc.), (ii) assembly language, (iii) object code generated from source code by a compiler, (iv) source code written using syntax from any suitable programming language for execution by an interpreter, (v) source code for compilation and execution by a just-in-time compiler, etc. Alternatively, the machine-readable instructions may be written in a hardware description language, such as logic implemented via either an FPGA configuration or an ASIC, or their equivalents. Accordingly, the functionality described herein may be implemented in any conventional computer programming language, as pre-programmed hardware elements, or as a combination of hardware and software components.

While the blocks shown in FIG. 5 are shown as all-occurring and in a particular order, in other embodiments, one or more of the blocks may not be performed, and in some embodiments, one or more of the blocks may be performed in a different order as shown and described herein.

Referring to FIG. 5 in conjunction with FIGS. 1, 2A-2B, and 3A-3B, at block 505, the identifier module 50 of the SHM system 20 identifies the vehicle 30 and/or the one or more composite components 32 based on identifying indicia 195 of the vehicle 30 and/or the one or more composite components 32. As a non-limiting example, the vehicle identifier module 52 of the identifier module 50 may obtain image data of the identifying indicia 195 of the vehicle 30 using an imaging device. The identifying indicia 195 may include a vehicle identification number (VIN), a bar code, an RFID tag, a make of the vehicle 30, a model of the vehicle 30, a shape of the vehicle 30, and/or other distinguishing characteristic of the vehicle 30. Subsequently, the vehicle identifier module 52 of the identifier module 50 may execute various image processing algorithms to identify the vehicle 30. As a non-limiting example, the vehicle identifier module 52 may obtain an image of a VIN of the vehicle 30 and identify, using an image processing algorithm, the vehicle 30 based on the VIN.

Furthermore, the component identifier module 54 of the identifier module 50 may scan the identifying indicia 195 of one or more composite components 32. Subsequently, the component identifier module 54 of the identifier module 50 may determine, based on the scanned data, a type of the one or more composite components 32 and any distinguishing characteristics associated with the one or more composite components 32, such as a geometry, dimensions, color, component type, nanoparticle type, and so on. As a non-limiting example, the component identifier module 54 may scan an RFID tag of the vehicle 30 and identify that the composite component 32 is a vehicle chassis including a plurality of quantum dots based on the scanned RFID tag.

Accordingly, the identifier module 50 may identify the component identification information by correlating the identifying indicia 195 of the vehicle 30 with the composite component 32 identified by the component identifier module 54, the type of the one or more nanoparticles 38 deposited on and/or embedded within the particular composite component 32, and the first reference entry associated with the particular composite component 32 of the identified vehicle 30. Moreover, the identifier module 50 may provide the component identification information to the SHM hardware selector module 60.

Still referring to FIG. 5 in conjunction with FIGS. 1, 2A-2B, and 3A-3B, at block 510, the SHM hardware selector module 60 of the SHM system 20 selects one of the SHM hardware subsystems 22. As described above, the SHM hardware selector module 60 may receive the component identification information from the identifier module 50. Moreover, the SHM hardware selector module 60 may determine that the nanoparticle type of the one or more composite components 32 (that is, the type of the one or more nanoparticles 38 embedded in and/or deposited on the one or more composite components 32) is a plurality of quantum dots based on the component identification information. Accordingly, the SHM hardware selector module 60 may retrieve a first entry of the plurality of entries of the SHM selector database 100, where the first entry includes information that correlates the nanoparticle type to one of the SHM hardware subsystems 22, such as the first SHM hardware subsystem 22-1. Accordingly, the first SHM hardware subsystem 22-1 includes a corresponding sensor system 24 for obtaining sensor data indicating the displacement of the plurality of quantum dots, as described below in further detail.

Still referring to FIG. 5 in conjunction with FIGS. 1, 2A-2B, and 3A-3B, at block 515, the SHM system 20 initiates the testing protocol based on the selected SHM hardware subsystems 22. In one or more embodiments, the testing protocol may be initiated by activating the selected SHM hardware subsystems 22, such as the first SHM hardware subsystem 22-1. In one or more embodiments, the testing protocol may be initiated by instructing, using the vehicle instruction module 70, an operator of the vehicle 30 to position the vehicle 30 such that the selected SHM hardware subsystems 22 can accurately obtain sensor data.

Furthermore, at block 515, the measurement event counter module 80 increases a testing iteration value of the one or more composite components 32 and/or the vehicle 30 and generates an entry that is stored in the measurement event database 110. As a non-limiting example, each entry of the measurement event database 110 indicates a number of iterations in which the one or more composite components 32 and/or the vehicle 30 have undergone the digital image correlation testing. As a non-limiting example, the testing iteration value may be one, two, three, four, and so on.

Still referring to FIG. 5 in conjunction with FIGS. 1, 2A-2B, and 3A-3B, at block 520, the corresponding sensor systems 24 of the selected SHM hardware subsystems 22 (the first SHM hardware subsystem 22-1) obtain sensor data of the one or more composite components 32 and determine a position of the one or more nanoparticles 38 based on the sensor data. As a non-limiting example and as described above, the first SHM hardware subsystems 22-1 may include a UV light source that provides an electromagnetic wave to the one or more composite components 32. Accordingly, when the one or more nanoparticles 38 are fluorescent polymer nanoparticles and/or the quantum dots, one or more cameras of the first sensor system 24-1 may capture the light emitted by the one or more nanoparticles 38 and determine the corresponding position of the one or more nanoparticles 38 within and/or on the one or more composite components 32 based on the corresponding image data.

Referring to FIG. 5 in conjunction with FIGS. 1, 2A-2B, 3A-3B, and 6A-6B, at block 525, the damage value determination module 90 determines a displacement of the one or more nanoparticles 38 based on a reference entry of the reference database 120. The displacement of the one or more nanoparticles 38 refers to a distance between a position of one or more nanoparticles and a corresponding reference position of the one or more nanoparticles.

As described above, the first reference entry may be generated during a manufacturing process of the one or more composite components 32 and/or the vehicle 30 (that is, when the one or more nanoparticles 38 are deposited on and/or embedded within the one or more composite components 32). As a non-limiting example, upon completion of a manufacture process of a composite component 32, one of sensor systems of the corresponding SHM hardware subsystems 22 obtains reference sensor data of the composite component 32. The reference sensor data, which indicates the position of the one or more nanoparticles 38 of the composite component 32, the type of the one or more nanoparticles 38 is associated with the component identification information of the composite component 32, and is subsequently utilized to generate the first reference entry. It should be understood that in some embodiments, the reference sensor data may be generated when each of the one or more composite components 32 are positioned within the vehicle 30 or when the vehicle 30 is assembled.

Figure 6A:
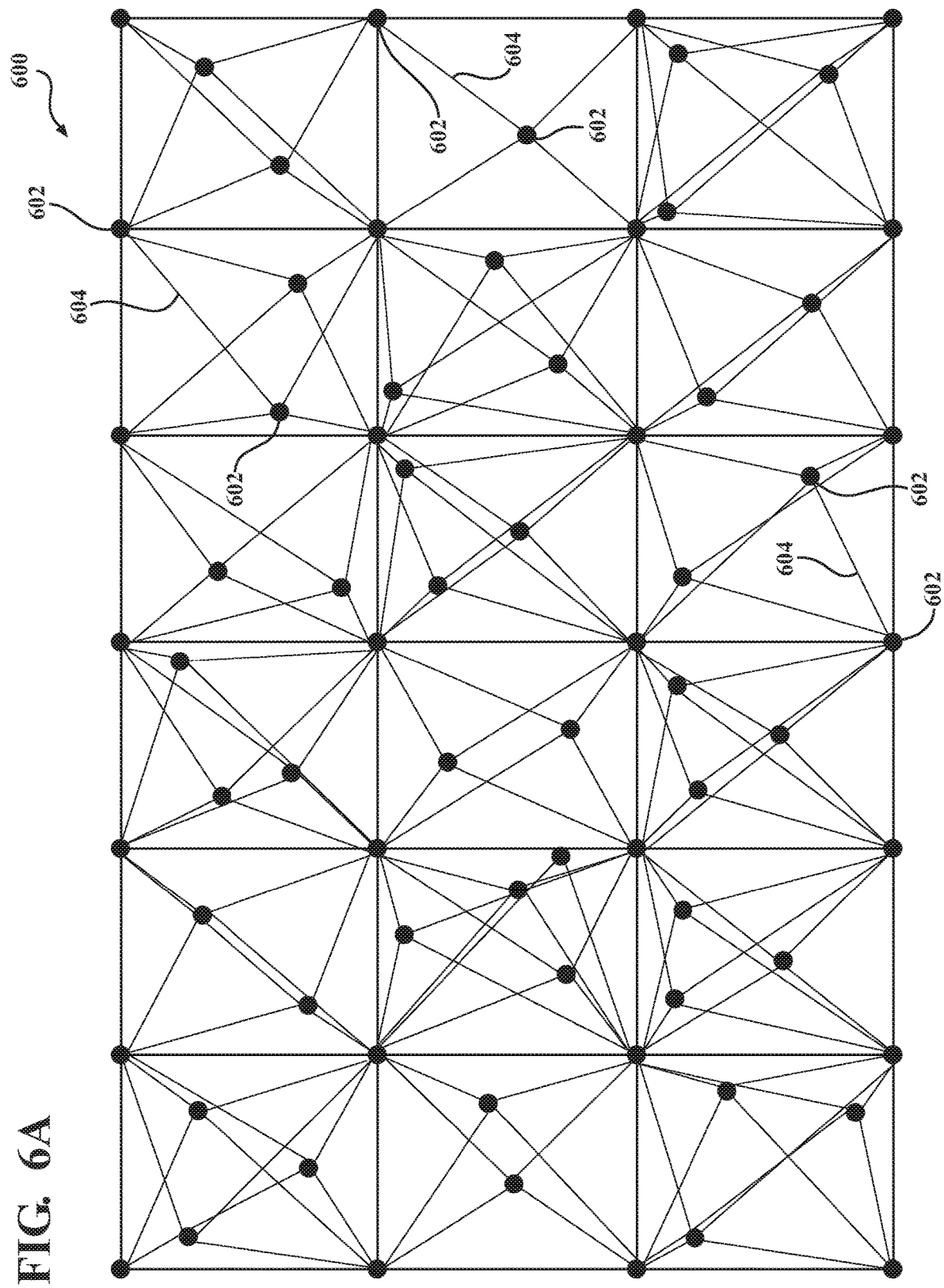
FIG. 6A schematically depicts an example illustration of a reference position of one or more nanoparticles of the composite component according to one or more embodiments shown and described herein.

In some embodiments and as illustrated in FIG. 6A, the first reference entry may include an image 600 indicating one or more reference positions 602 of the one or more nanoparticles 38. Additionally, the image 600 may include one or more distance markers 604 indicating a reference displacement between each of the one or more nanoparticles 38. While the one or more distance markers 604 are illustrated as lines, it should be understood that the one or more distance markers 604 may include text, characters, and/or other graphics indicating the reference displacement between each of the one or more nanoparticles 38.

Figure 6B:
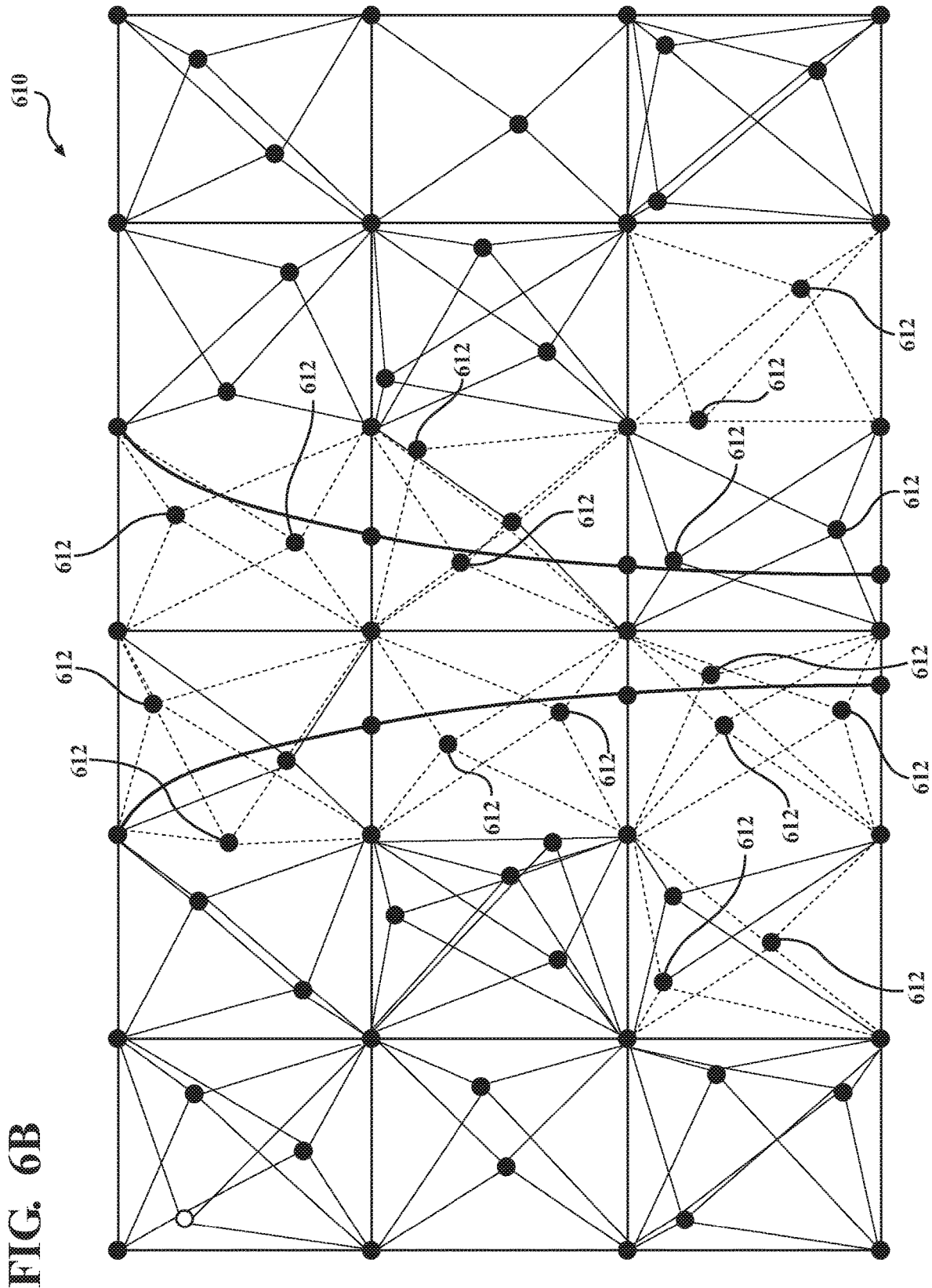
FIG. 6B schematically depicts an example illustration of a displacement of one or more nanoparticles of the composite component according to one or more embodiments shown and described herein.

Accordingly, the damage value determination module 90 may determine a displacement of the one or more nanoparticles 38 by generating an image 610 representing the sensor data obtained by the corresponding SHM hardware subsystem 22, as shown in FIG. 6B, and comparing the image 610 to the image 600 to determine the displacement. As a non-limiting example and as shown in FIG. 6B, the one or more positions 612 of the one or more nanoparticles 38 in image 610 indicate that the one or more nanoparticles 38 have been displaced. Subsequently, the displacement of the one or more nanoparticles 38 may be determined using, for example, various image processing algorithms, such as DIC, that overlay and compare image 600 and image 610.

Referring to FIG. 5 in conjunction with FIGS. 1, 2A-2B, and 3A-3B, at block 530, the damage value determination module 90 determines a damage value of the one or more nanoparticles 38 based on displacement of the one or more nanoparticles 38. As a non-limiting example, the damage value may be based on an average displacement of each of the one or more nanoparticles 38, a median displacement of each of the one or more nanoparticles 38, a maximum displacement of each of the one or more nanoparticles 38, a minimum displacement of each of the one or more nanoparticles 38, and/or other similar arithmetic representation of the displacement of the one or more nanoparticles 38.

Referring to FIG. 5 in conjunction with FIGS. 1, 2A-2B, and 3A-3B, at block 535, the damage value determination module 90 determines a damage threshold based on at least one of the measurement event database 110 and the historical damage database 130. In one or more embodiments, the damage value determination module 90 may obtain the testing iteration value of the one or more composite components 32 and/or the vehicle 30 from the measurement event database 110. Subsequently, the damage value determination module 90 identifies an entry from the historical damage database 130 that correlates the testing iteration value to an expected displacement value of the one or more composite components 32 and/or the vehicle 30. As a non-limiting example, during an annual testing protocol of the vehicle 30, the testing iteration value may be ten. As such, the testing iteration value may indicate that the vehicle 30 is at least ten years old. Accordingly, the damage value determination module 90 may identify an entry in the historical damage database 130 that predicts an expected displacement value of the one or more nanoparticles 38 based on, for example, prior damage value measurements, normal wear and tear, expected impact forces, and/or any other events that may cause the one or more nanoparticles 38. Therefore, the damage threshold may be relatively higher if the testing iteration value as indicated by the corresponding measurement event database 110 is higher, and the damage threshold may be relatively lower if the testing iteration value is lower.

Referring to FIG. 5 in conjunction with FIGS. 1, 2A-2B, and 3A-3B, at block 540, the damage value determination module 90 determines whether the damage value is greater than the damage threshold value. If so, the method 500 proceeds to block 545; otherwise, the method 500 proceeds to block 550.

Still referring to FIG. 5 in conjunction with FIGS. 1, 2A-2B, and 3A-3B, at block 545, the damage value determination module 90 transmits a notification indicating that the vehicle 30 and/or the one or more composite components 32 are damaged and then proceeds to block 555. As a non-limiting example, the notification may cause the notification unit 42, which may include a display, to generate a graphic including text, images, shapes, heat maps, and/or the like indicating a severity and/or location of the damage of the one or more composite components 32 of the vehicle 30.

Still referring to FIG. 5 in conjunction with FIGS. 1, 2A-2B, and 3A-3B, when the determination is NO at block 540, the process proceeds to block 550 where the damage value determination module 90 transmits a notification indicating that the damage value is less than the expected damage value (that is, the one or more composite components 32 and/or the vehicle 30 are undamaged) and then proceeds to block 555. As a non-limiting example, the notification may cause the remote computing system 40 and/or a display device communicatively coupled to the SHM system 20 to generate a graphic including text, images, shapes, heat maps, and/or the like indicating that the damage value is less than the expected damage value. At block 555, the damage value determination module 90 updates the historical damage database 130 based on the determined damage value and then ends.

It should now be understood that embodiments of the present disclosure are directed to systems and methods for determining a damage value of the one or more composite components 32 and/or the vehicle. By performing a digital image correlation to evaluate a displacement of the one or more nanoparticles 38 positioned on and/or embedded within the one or more composite components 32, the SHM system 20 to accurately identify and detect damage to the one or more composite components 32 of the vehicle 30 that may otherwise not be readily discernable to the naked eye of a user.

In a first aspect of the present disclosure, a structural health monitoring method includes obtaining, using one or more processors, component identification information associated with a composite component, the composite component includes a matrix and a reinforcement. The structural health monitoring method includes obtaining, using one or more sensors, sensor data of the composite component, where the sensor data of the composite component indicates a position of one or more nanoparticles, the one or more nanoparticles are at least one of deposited on the composite component and embedded within the composite component. The structural health monitoring method includes identifying, using the one or more processors, a first reference entry of a plurality of reference entries in a reference database corresponding to the component identification information, where the first reference entry indicates a reference position of the one or more nanoparticles. The structural health monitoring method includes executing, using the one or more processors, a digital image correlation between the sensor data and the first reference entry of the plurality of reference entries. The structural health monitoring method includes determining, using the one or more processors, a damage value of the composite component based on the digital image correlation between the sensor data and the first reference entry.

A second aspect of the present disclosure may include the first aspect, where executing the digital image correlation between the sensor data and the first reference entry of the plurality of reference entries further includes determining, using the one or more processors, a displacement of the one or more nanoparticles, the displacement indicating a distance between the position of the one or more nanoparticles and the reference position of the one or more nanoparticles.

A third aspect of the present disclosure may include any one of the first or second aspects, in which the method further comprises determining, using the one or more processors, whether the damage value is greater than a threshold value. The method further comprises transmitting, using the one or more processors, a notification in response to the damage value being greater than the threshold value.

A fourth aspect of the present disclosure may include any one of the first through third aspects, in which the method further comprises identifying, using the one or more processors, a first measurement event entry in a measurement event database, the first measurement event entry corresponding to a testing iteration value of the composite component. The method further comprises identifying, using the one or more processors, a first historical damage entry in a historical damage database, the first historical damage entry indicates an estimated damage value based on the first measurement event entry. The method further comprises determining, using the one or more processors, the threshold value based on the first historical damage entry.

A fifth aspect of the present disclosure may include any one of the first through fourth aspects, where obtaining the sensor data of the composite component further comprises selecting, using the one or more processors, a first set of the one or more sensors based on the component identification information associated with the composite component. Obtaining the sensor data of the composite component further comprises obtaining, using the first set of the one or more sensors, the sensor data of the composite component.

A sixth aspect of the present disclosure may include any one of the first through fifth aspects, where the one or more nanoparticles are one or more magnetic nanoparticles.

A seventh aspect of the present disclosure may include any one of the first through sixth aspects, where the one or more nanoparticles are one or more fluorescent polymer particles.

An eighth aspect of the present disclosure may include any one of the first through seventh aspects, where the one or more nanoparticles are one or more quantum dots.

A ninth aspect of the present disclosure may include any one of the first through eighth aspects, where the composite component is a vehicle component, and where the component identification information is associated with the vehicle component.

A tenth aspect of the present disclosure may include any one of the first through ninth aspects, where the vehicle component is a vehicle chassis.

In an eleventh aspect of the present disclosure, a system includes one or more processors and one or more non-transitory memory modules communicatively coupled to the one or more processors and storing machine-readable instructions. Executing the machine-readable instructions causes the one or more processors to identify indicia associated with a composite component, the indicia including component identification information, the composite component includes a matrix and a reinforcement. Executing the machine-readable instructions causes the one or more processors to obtain sensor data of the composite component, where the sensor data of the composite component indicates a position of one or more nanoparticles that are at least one of deposited on the composite component and embedded within the composite component. Executing the machine-readable instructions causes the one or more processors to identify a first reference entry of a plurality of reference entries in a reference database based on the indicia, where the first reference entry indicates a reference position of the one or more nanoparticles. Executing the machine-readable instructions causes the one or more processors to execute a digital image correlation between the sensor data and the first reference entry of the plurality of reference entries.

Executing the machine-readable instructions causes the one or more processors to determine a damage value of the composite component based on the digital image correlation between the sensor data and the first reference entry.

A twelfth aspect of the present disclosure may include the eleventh aspect, where executing the digital image correlation between the sensor data and the first reference entry of the plurality of reference entries further causes the one or more processors to determine a displacement of the one or more nanoparticles, the displacement indicating a distance between the position of the one or more nanoparticles and the reference position of the one or more nanoparticles.

A thirteenth aspect of the present disclosure may include any one of the eleventh or twelfth aspects, in which the machine-readable instructions, when executed, cause the one or more processors to determine whether the damage value is greater than a threshold value. The machine-readable instructions, when executed, cause the one or more processors to transmit a notification in response to the damage value being greater than the threshold value.

A fourteenth aspect of the present disclosure may include any one of the eleventh through thirteenth aspects, in which the machine-readable instructions, when executed, cause the one or more processors to identify a first measurement event entry in a measurement event database, the first measurement event entry corresponding to a testing iteration value of the composite component. The machine-readable instructions, when executed, cause the one or more processors to identify a first historical damage entry in a historical damage database, the first historical damage entry indicates an estimated damage value based on the first measurement event entry. The machine-readable instructions, when executed, cause the one or more processors to determine the threshold value based on the first historical damage entry.

A fifteenth aspect of the present disclosure may include any one of the eleventh through fourteenth aspects, where obtaining the sensor data of the composite component further causes the one or more processors to select a first set of the one or more sensors based on the component identification information associated with the composite component. Obtaining the sensor data of the composite component further causes the one or more processors to obtain using the first set of the one or more sensors, the sensor data of the composite component.

A sixteenth aspect of the present disclosure may include any one of the eleventh through fifteenth aspects, where the one or more nanoparticles are one or more magnetic nanoparticles.

A seventeenth aspect of the present disclosure may include any one of the eleventh through sixteenth aspects, where the one or more nanoparticles are one or more fluorescent polymer particles.

An eighteenth aspect of the present disclosure may include any one of the eleventh through seventeenth aspects, where the one or more nanoparticles are one or more quantum dots.

A nineteenth aspect of the present disclosure may include any one of the eleventh through eighteenth aspects, where the composite component is a vehicle component, and where the component identification information is associated with the vehicle component.

A twentieth aspect of the present disclosure may include any one of the eleventh through nineteenth aspects, where the vehicle component is a vehicle chassis.

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the disclosure should be construed to include everything within the scope of the appended claims and their equivalents.

The invention claimed is:

1. A structural health monitoring method comprising:
  obtaining, using one or more processors, component identification information associated with a composite component, the composite component includes a matrix and a reinforcement;
  determining, using the one or more processors, a nanoparticle type of one or more nanoparticles embedded within the composite component based on the component identification information;
  selecting, using the one or more processors, one or more sensors for detecting the nanoparticle type based on the determined nanoparticle type;
  obtaining, using the selected one or more sensors, sensor data of the composite component, the sensor data of the composite component indicates a position of the one or more nanoparticles embedded within the composite component;
  identifying, using the one or more processors, a first reference entry of a plurality of reference entries in a reference database corresponding to the component identification information, the first reference entry indicates a reference position of the one or more nanoparticles;
  executing, using the one or more processors, a digital image correlation between the sensor data and the first reference entry of the plurality of reference entries; and
  determining, using the one or more processors, a damage value of the composite component based on the digital image correlation between the sensor data and the first reference entry.

2. The structural health monitoring method of claim 1, where executing the digital image correlation between the sensor data and the first reference entry of the plurality of reference entries further comprises determining, using the one or more processors, a displacement of the one or more nanoparticles, the displacement indicating a distance between the position of the one or more nanoparticles and the reference position of the one or more nanoparticles.

3. The structural health monitoring method of claim 1, further comprising:
  determining, using the one or more processors, whether the damage value is greater than a threshold value; and
  transmitting, using the one or more processors, a notification in response to the damage value being greater than the threshold value.

4. The structural health monitoring method of claim 3, further comprising:
  identifying, using the one or more processors, a first measurement event entry in a measurement event database, the first measurement event entry corresponding to a testing iteration value of the composite component;
  identifying, using the one or more processors, a first historical damage entry in a historical damage database, the first historical damage entry indicates an estimated damage value based on the first measurement event entry; and
  determining, using the one or more processors, the threshold value based on the first historical damage entry.

5. The structural health monitoring method of claim 1, where the one or more nanoparticles are one or more magnetic nanoparticles.

6. The structural health monitoring method of claim 1, where the one or more nanoparticles are one or more fluorescent polymer particles.

7. The structural health monitoring method of claim 1, where the one or more nanoparticles are one or more quantum dots.

8. The structural health monitoring method of claim 1, where:
the composite component is a vehicle component; and
the component identification information is associated with the vehicle component.

9. The structural health monitoring method of claim 8, where the vehicle component is a vehicle chassis.

10. A system comprising:
one or more processors; and
one or more non-transitory memories communicatively coupled to the one or more processors and storing machine-readable instructions that, when executed, cause the one or more processors to:
identify indicia associated with a composite component, the indicia including component identification information, the composite component includes a matrix and a reinforcement;
determine a nanoparticle type of one or more nanoparticles embedded within the composite component based on the component identification information;
select one or more sensors for detecting the nanoparticle type based on the determined nanoparticle type;
obtain sensor data of the composite component from the selected one or more sensors, the sensor data of the composite component indicates a position of one or more nanoparticles that are embedded within the composite component;
identify a first reference entry of a plurality of reference entries in a reference database based on the indicia, the first reference entry indicates a reference position of the one or more nanoparticles;
execute a digital image correlation between the sensor data and the first reference entry of the plurality of reference entries; and
determine a damage value of the composite component based on the digital image correlation between the sensor data and the first reference entry.

11. The system of claim 10, where executing the digital image correlation between the sensor data and the first reference entry of the plurality of reference entries further causes the one or more processors to determine a displacement of the one or more nanoparticles, the displacement indicating a distance between the position of the one or more nanoparticles and the reference position of the one or more nanoparticles.

12. The system of claim 10, where the machine-readable instructions, when executed, cause the one or more processors to:
determine whether the damage value is greater than a threshold value; and
transmit a notification in response to the damage value being greater than the threshold value.

13. The system of claim 12, where the machine-readable instructions, when executed, cause the one or more processors to:
identify a first measurement event entry in a measurement event database, the first measurement event entry corresponding to a testing iteration value of the composite component;
identify a first historical damage entry in a historical damage database, the first historical damage entry indicates an estimated damage value based on the first measurement event entry; and
determine the threshold value based on the first historical damage entry.

14. The system of claim 10, where the one or more nanoparticles are one or more magnetic nanoparticles.

15. The system of claim 10, where the one or more nanoparticles are one or more fluorescent polymer particles.

16. The system of claim 10, where the one or more nanoparticles are one or more quantum dots.

17. The system of claim 10, where:
the composite component is a vehicle component; and
the component identification information is associated with the vehicle component.

18. The system of claim 17, where the vehicle component is a vehicle chassis.

* * * * *